US010758615B2

(12) United States Patent
Couvineau et al.

(10) Patent No.: US 10,758,615 B2
(45) Date of Patent: Sep. 1, 2020

(54) HUMAN MONOCLONAL ANTIBODIES AGAINST OREXIN RECEPTOR TYPE 1

(71) Applicants: INSERM (INSTITUT NATIONAL DE LA SANTE ET DE LA RECHERCHE MEDICALE), Paris (FR); UNIVERSITE PARIS DIDEROT—PARIS 7, Paris (FR); INSTITUT REGIONAL DU CANCER DE MONTPELLIER, Montpellier (FR); UNIVERSITE DE MONTPELLIER, Montpellier (FR)

(72) Inventors: Alain Couvineau, Paris (FR); Thierry Voisin, Paris (FR); Pascal Nicole, Paris (FR); Bruno Robert, Montpellier (FR); Pierre Martineau, Montpellier (FR); Myriam Chentouf, Montpellier (FR)

(73) Assignees: INSERM (INSTITUT NATIONAL DE LA SANTA ET DE LA RECHERCHE MEDICALE), Paris (FR); UNIVERSITE PARIS DIDEROT—PARIS 7, Paris (FR); INSTITUT REGIONAL DU CANCER DE MONTPELLIER, Montpellier (FR); UNIVERSITE DE MONTPELLIER, Montpellier (FR)

( * ) Notice: Subject to any disclaimer, the term of this patent is extended or adjusted under 35 U.S.C. 154(b) by 224 days.

(21) Appl. No.: 15/543,371

(22) PCT Filed: Jan. 14, 2016

(86) PCT No.: PCT/EP2016/050677
§ 371 (c)(1),
(2) Date: Jul. 13, 2017

(87) PCT Pub. No.: WO2016/113356
PCT Pub. Date: Jul. 21, 2016

(65) Prior Publication Data
US 2018/0002421 A1 Jan. 4, 2018

(30) Foreign Application Priority Data
Jan. 16, 2015 (EP) .................................... 15305038

(51) Int. Cl.
| A61K 39/395 | (2006.01) |
| C07K 16/30 | (2006.01) |
| A61P 35/00 | (2006.01) |
| C12N 15/85 | (2006.01) |
| C07K 16/28 | (2006.01) |
| A61K 39/00 | (2006.01) |

(52) U.S. Cl.
CPC ...... *A61K 39/39558* (2013.01); *C07K 16/286* (2013.01); *C07K 16/30* (2013.01); *A61K 2039/505* (2013.01); *C07K 2317/21* (2013.01); *C07K 2317/73* (2013.01)

(58) Field of Classification Search
None
See application file for complete search history.

(56) References Cited

U.S. PATENT DOCUMENTS

2017/0319661 A1* 11/2017 Chartrel ........... C07K 14/70571

FOREIGN PATENT DOCUMENTS

WO 2011/050199 A1 4/2011

OTHER PUBLICATIONS

Rudikoff et al.(Proceedings of the National Academy of Sciences USA, vol. 79, p. 1979-1983, 1982) (Year: 1982).*
Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Rudikoff et al. (Proc Natl Acad Sci USA 79: 1979-1983, 1982) (Year: 1982).*
Portolano (The Journal of Immunology, vol. 150, No. 3, p. 880-887, 1993) (Year: 1993).*
Klimka (British Journal of Cancer (2000) 83: 252-260) (Year: 2000).*
Beiboer (J. Mol. Biol. (2000) 296:833-849) (Year: 2000).*
Yuko Mihara et al: "Expression and Localization of the Orexin-1 Receptor (OX1R) After Traumatic Brain Injury in Mice", Journal of Molecular Neuroscience, vol. 43, No. 2, pp. 162-168, Aug. 28, 2010.

* cited by examiner

Primary Examiner — Michael Allen
(74) Attorney, Agent, or Firm — W&C IP

(57) ABSTRACT

The present disclosure relates to human monoclonal antibodies against orexin receptor type 1 (OX1R, hyprocretin 1) and uses thereof for the treatment of cancer. The antibodies are characterized by their CDRs: NYYMN, YISGSSRNIYYADFVKG, SNYDGMDV (Heavy chain) and AGTSSDVGGSNYVS, PGKAP, SSYTYYSTRV (Light Chain)) or the CDRS having at least 50% or 70% identity with the above listed sequences.

Figure 1:
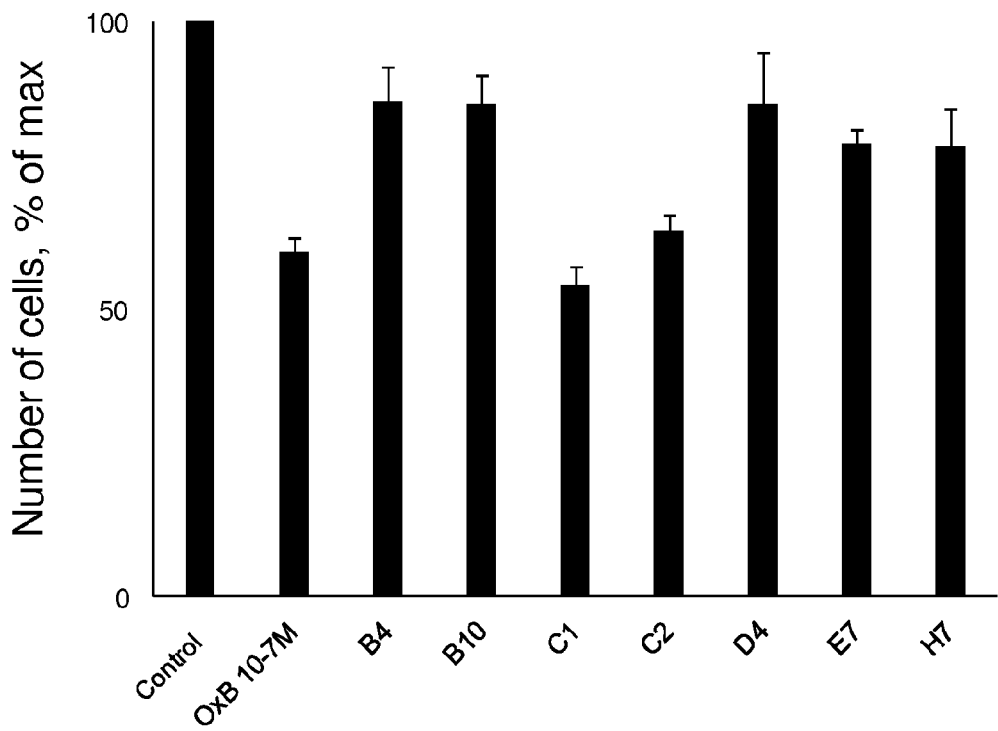

14 Claims, 7 Drawing Sheets
Specification includes a Sequence Listing.

SEQUENCE LISTING

<160> NUMBER OF SEQ ID NOS: 9

<210> SEQ ID NO 1
<211> LENGTH: 120
<212> TYPE: PRT
<213> ORGANISM: Artificial

```
<220> FEATURE:
<223> OTHER INFORMATION: Synthetic VH sequence of C2

<400> SEQUENCE: 1

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Ser
            20                  25                  30

Tyr Met Asn Trp Val Arg Gln Ala Pro Gly Lys Gly Leu Glu Trp Ile
        35                  40                  45

Ser Ser Ile Tyr Gly Ser Ser Arg Tyr Ile Asp Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Ser Ser Tyr Tyr Gly Ser Gly Met Asp Val Trp Gly Arg
            100                 105                 110

Gly Thr Leu Val Thr Val Ser Ser
        115                 120

<210> SEQ ID NO 2
<211> LENGTH: 111
<212> TYPE: PRT
<213> ORGANISM: Artificial
<220> FEATURE:
<223> OTHER INFORMATION: Synthetic VL sequence of C2

<400> SEQUENCE: 2

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Gly Ser Val Ser Trp Tyr Gln Gln His Pro Gly Lys Ala Pro Lys Leu
        35                  40                  45

Met Ile Tyr Tyr Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Asn Thr Asn Ser
                85                  90                  95

Ser Thr Arg Val Phe Gly Gly Gly Thr Lys Leu Ala Val Leu Gly
            100                 105                 110

<210> SEQ ID NO 3
<211> LENGTH: 5
<212> TYPE: PRT
<213> ORGANISM: Artificial Sequence
<220> FEATURE:
<223> OTHER INFORMATION: Synthetic heavy chain CDR

<400> SEQUENCE: 3

Asn Ser Tyr Met Asn
1               5

<210> SEQ ID NO 4
<211> LENGTH: 17
<212> TYPE: PRT
<213> ORGANISM: Artificial Sequence
<220> FEATURE:
```

```
<223> OTHER INFORMATION: Synthetic heavy chain CDR

<400> SEQUENCE: 4

Ser Ile Tyr Gly Ser Ser Arg Tyr Ile Asp Tyr Ala Asp Phe Val Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: Synthetic heavy chain CDR

<400> SEQUENCE: 5

Ser Ser Ser Tyr Tyr Gly Ser Gly Met Asp Val
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic light chain CDR

<400> SEQUENCE: 6

Ala Gly Thr Ser Ser Asp Val Gly Gly Ser Asn Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic light chain CDR

<400> SEQUENCE: 7

Tyr Asp Ser Tyr Arg Pro Ser
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic light chain CDR

<400> SEQUENCE: 8

Ser Ser Tyr Thr Tyr Tyr Ser Thr Arg Val
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Synthetic motif

<400> SEQUENCE: 9

Cys Pro Pro Cys
1
```

HUMAN MONOCLONAL ANTIBODIES AGAINST OREXIN RECEPTOR TYPE 1

FIELD OF THE PRESENT INVENTION

The present invention relates to human monoclonal antibodies against orexin receptor type 1 (OX1R) and uses thereof for the treatment of cancer.

BACKGROUND OF THE PRESENT INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour. Orexins regulate states of sleep and wakefulness opening potentially novel therapeutic approaches for narcoleptic or insomniac patients. Orexins have also been indicated as playing a role in arousal, reward, learning and memory. Two orexin receptors have been cloned and characterized in mammals. They belong to the super family of G-protein coupled receptors (7-transmembrane spanning receptor) (Sakurai T. et al., Cell, 1998, 92, 573-585): the orexin-1 receptor (OX1R or HCTR1) is more selective for OX-A than OX-B and the orexin-2 receptor (OX2R or HCTR2) binds OX-A as well as OX-B. A recent study shows that activation of OX1R by orexin can promote robust in vitro and in vivo apoptosis in colon cancer cells even when they are resistant to the most commonly used drug in colon cancer chemotherapy (Voisin T, El Firar A, Fasseu M, Rouyer-Fessard C, Descatoire V, Walker F, Paradis V, Bedossa P, Henin D, Lehy T, Laburthe M. Aberrant expression of OX1 receptors for orexins in colon cancers and liver metastases: an openable gate to apoptosis. Cancer Res. 2011 May 1; 71(9):3341-51). In particular, it was shown that OX1R promotes apoptosis in the cancer cell lines through a mechanism which is not related to Gq-mediated phospholipase C activation and cellular calcium transients. Orexins induce indeed tyrosine phosphorylation of 2 tyrosine-based motifs in OX1R, ITIM and ITSM, resulting in the recruitment of the phosphotyrosine phosphatase SHP-2, the activation of which is responsible for mitochondrial apoptosis (Voisin T, El Firar A, Rouyer-Fessard C, Gratio V, Laburthe M. A hallmark of immunoreceptor, the tyrosine-based inhibitory motif ITIM, is present in the G protein-coupled receptor OX1R for orexins and drives apoptosis: a novel mechanism. FASEB J. 2008 Jun.; 22(6):1993-2002.; El Firar A, Voisin T, Rouyer-Fessard C, Ostuni M A, Couvineau A, Laburthe M. Discovery of a functional immunoreceptor tyrosine-based switch motif in a 7-transmembrane-spanning receptor: role in the orexin receptor OX1R-driven apoptosis. FASEB J. 2009 Dec.; 23(12):4069-80. doi: 10.1096/fj.09-131367. Epub 2009 Aug. 6). Remarkably, all primary colorectal tumors regardless of their localization and Duke's stages expressed OX1R while adjacent normal colonocytes as well as control normal tissues were negative. Besides, expression of OX1R has been recently confirmed in pancreatic cancer, hepatocarcimomas, and advanced prostate cancer. Accordingly the prior art supports that OX1R is an Achilles's heel of cancers (even chemoresistance) and suggests that OX1R is a relevant target for cancer therapy. However, antibodies against OX1R that are capable of promoting apoptosis of cancer cells have never been described in the prior art.

SUMMARY OF THE PRESENT INVENTION

The present invention relates to human monoclonal antibodies against orexin receptor type 1 (OX1R) and uses thereof for the treatment of cancer. In particular, the present invention is defined by the claims.

DETAILED DESCRIPTION OF THE PRESENT INVENTION

The present invention provides human monoclonal antibodies against OX1R. In particular, the human monoclonal antibodies of the present invention are characterized by one or more functional properties such that they are human antibodies, bind with high affinity to human OX1R, are able to cross react between the murine and human form of OX1R, and are capable of promoting apoptosis of cancer cells and in vivo inhibition of tumor development. In particular, the present invention provides antibodies that derive from the C2 antibody as described in the EXAMPLE.

As used herein the term "OX1R" has its general meaning in the art and refers to orexin receptor type, also known as hypocretin receptor type 1, which is a protein that in humans is encoded by the HCRTR1 gene. According to the present invention, OX1R promotes apoptosis in the various cancer cell lines through a mechanism which is not related to Gq-mediated phopholipase C activation and cellular calcium transients. Orexins induce indeed tyrosine phosphorylation of 2 tyrosine-based motifs in OX1R, ITIM and ITSM, resulting in the recruitment of the phosphotyrosine phosphatase SHP-2, the activation of which is responsible for mitochondrial apoptosis (Voisin T, El Firar A, Rouyer-Fessard C, Gratio V, Laburthe M. A hallmark of immunoreceptor, the tyrosine-based inhibitory motif ITIM, is present in the G protein-coupled receptor OX1R for orexins and drives apoptosis: a novel mechanism. FASEB J. 2008 Jun.; 22(6):1993-2002.; El Firar A, Voisin T, Rouyer-Fessard C, Ostuni M A, Couvineau A, Laburthe M. Discovery of a functional immunoreceptor tyrosine-based switch motif in a 7-transmembrane-spanning receptor: role in the orexin receptor OX1R-driven apoptosis. FASEB J. 2009 Dec.; 23(12):4069-80. doi: 10.1096/fj.09-131367. Epub 2009 Aug. 6.). Human antibodies of the present invention are thought to be capable of promoting apoptosis of cancer cells via the same mechanism.

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

As used herein the term "human antibody" as used herein, is intended to include antibodies having variable and constant regions derived from human immunoglobulin sequences. The human antibodies of the present invention may include amino acid residues not encoded by human immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

According to the present invention, the VH region of the C2 antibody consists of the sequence of SEQ ID NO:1 which is defined as follows and the kabat numbered sequence is defined in Table A.

SEQ ID NO: 1
EVQLVESGGSLVKPGGSLRLSCAASGFTFSNSYMNWVRQAPGKGLEWISS

IYGSSRYIDYADFVKGRFTISRDNATNSLYLQMNSLRAEDTAVYYCVRSS

SYYGSGMDVWGRGTLVTVSS

TABLE A kabat numbered sequence of the VH domain of C2

| Position in SEQ ID NO: 1 | Kabat numbering | Amino acid |
|---|---|---|
| 1 | H1 | E |
| 2 | H2 | V |
| 3 | H3 | Q |
| 4 | H4 | L |
| 5 | H5 | V |
| 6 | H6 | E |
| 7 | H7 | S |
| 8 | H8 | G |
| 9 | H9 | G |
| 10 | H10 | S |
| 11 | H11 | L |
| 12 | H12 | V |
| 13 | H13 | K |
| 14 | H14 | P |
| 15 | H15 | G |
| 16 | H16 | G |
| 17 | H17 | S |
| 18 | H18 | L |
| 19 | H19 | R |
| 20 | H20 | L |
| 21 | H21 | S |
| 22 | H22 | C |
| 23 | H23 | A |
| 24 | H24 | A |
| 25 | H25 | S |
| 26 | H26 | G |
| 27 | H27 | F |
| 28 | H28 | T |
| 29 | H29 | F |
| 30 | H30 | S |
| 31 | H31 | N |
| 32 | H32 | S |
| 33 | H33 | Y |
| 34 | H34 | M |
| 35 | H35 | N |
| 36 | H36 | W |
| 37 | H37 | V |
| 38 | H38 | R |
| 39 | H39 | Q |
| 40 | H40 | A |
| 41 | H41 | P |
| 42 | H42 | G |
| 43 | H43 | K |
| 44 | H44 | G |
| 45 | H45 | L |
| 46 | H46 | E |
| 47 | H47 | W |
| 48 | H48 | I |
| 49 | H49 | S |

TABLE A-continued kabat numbered sequence of the VH domain of C2

| Position in SEQ ID NO: 1 | Kabat numbering | Amino acid |
|---|---|---|
| 50 | H50 | S |
| 51 | H51 | I |
| 52 | H52 | Y |
| 53 | H52A | G |
| 54 | H53 | S |
| 55 | H54 | S |
| 56 | H55 | R |
| 57 | H56 | Y |
| 58 | H57 | I |
| 59 | H58 | D |
| 60 | H59 | Y |
| 61 | H60 | A |
| 62 | H61 | D |
| 63 | H62 | F |
| 64 | H63 | V |
| 65 | H64 | K |
| 66 | H65 | G |
| 67 | H66 | R |
| 68 | H67 | F |
| 69 | H68 | T |
| 70 | H69 | I |
| 71 | H70 | S |
| 72 | H71 | R |
| 73 | H72 | D |
| 74 | H73 | N |
| 75 | H74 | A |
| 76 | H75 | T |
| 77 | H76 | N |
| 78 | H77 | S |
| 79 | H78 | L |
| 80 | H79 | Y |
| 81 | H80 | L |
| 82 | H81 | Q |
| 83 | H82 | M |
| 84 | H82A | N |
| 85 | H82B | S |
| 86 | H82C | L |
| 87 | H83 | R |
| 88 | H84 | A |
| 89 | H85 | E |
| 90 | H86 | D |
| 91 | H87 | T |
| 92 | H88 | A |
| 93 | H89 | V |
| 94 | H90 | Y |
| 95 | H91 | Y |
| 96 | H92 | C |
| 97 | H93 | V |
| 98 | H94 | R |
| 99 | H95 | S |
| 100 | H96 | S |
| 101 | H97 | S |
| 102 | H98 | Y |
| 103 | H99 | Y |
| 104 | H100 | G |
| 105 | H100A | S |
| 106 | H100B | G |
| 107 | H100C | M |
| 108 | H101 | D |
| 109 | H102 | V |
| 110 | H103 | W |
| 111 | H104 | G |
| 112 | H105 | R |
| 113 | H106 | G |
| 114 | H107 | T |
| 115 | H108 | L |
| 116 | H109 | V |
| 117 | H110 | T |
| 118 | H111 | V |
| 119 | H112 | S |
| 120 | H113 | S |

Accordingly, the H-CDR1 of C2 is defined by the sequence ranging from the amino acid residue at position 31 to the amino acid residue at position 35 in SEQ ID NO:1.

Accordingly, the H-CDR2 of C2 is defined by the sequence ranging from the amino acid residue at position 50 to the amino acid residue at position 66 in SEQ ID NO:1.

Accordingly, the H-CDR3 of C2 is defined by the sequence ranging from the amino acid residue at position 99 to the amino acid residue at position 109 in SEQ ID NO:1.

According to the present invention, the VL region of the C2 antibody consists of the sequence of SEQ ID NO:2 which is defined as follows and the kabat numbered sequence is defined in Table B.

SEQ ID NO: 2:
QSVLTQPASVSGSPGQSITISCAGTSSDVGGYGSVSWYQQHPGKAPKLMI

YYDSYRPSGVSNRFSGSKSGNTASLTISGLQAEDEADYYCSSNTNSSTRV

FGGGTKLAVLG

TABLE B kabat numbered sequence of the VL domain of C2

| Position in SEQ ID NO: 2 | Kabat numbering | Amino acid |
|---|---|---|
| 1 | L1 | Q |
| 2 | L2 | S |
| 3 | L3 | V |
| 4 | L4 | L |
| 5 | L5 | T |
| 6 | L6 | Q |
| 7 | L7 | P |
| 8 | L8 | A |
| 9 | L9 | S |
|  | L10 | — |
| 10 | L11 | V |
| 11 | L12 | S |
| 12 | L13 | G |
| 13 | L14 | S |
| 14 | L15 | P |
| 15 | L16 | G |
| 16 | L17 | Q |
| 17 | L18 | S |
| 18 | L19 | I |
| 19 | L20 | T |
| 20 | L21 | I |
| 21 | L22 | S |
| 22 | L23 | C |
| 23 | L24 | A |
| 24 | L25 | G |
| 25 | L26 | T |
| 26 | L27 | S |
| 27 | L27A | S |
| 28 | L27B | D |
| 29 | L27C | V |
| 30 | L28 | G |
| 31 | L29 | G |
| 32 | L30 | S |
| 33 | L31 | N |
| 34 | L32 | Y |
| 35 | L33 | V |
| 36 | L34 | S |
| 37 | L35 | W |
| 38 | L36 | Y |
| 39 | L37 | Q |
| 40 | L38 | Q |
| 41 | L39 | H |
| 42 | L40 | P |
| 43 | L41 | G |
| 44 | L42 | K |
| 45 | L43 | A |
| 46 | L44 | P |
| 47 | L45 | K |
| 48 | L46 | L |
| 49 | L47 | M |
| 50 | L48 | I |
| 51 | L49 | Y |
| 52 | L50 | S |

TABLE B-continued kabat numbered sequence of the VL domain of C2

| Position in SEQ ID NO: 2 | Kabat numbering | Amino acid |
|---|---|---|
| 53 | L51 | D |
| 54 | L52 | S |
| 55 | L53 | Y |
| 56 | L54 | R |
| 57 | L55 | P |
| 58 | L56 | S |
| 59 | L57 | G |
| 60 | L58 | V |
| 61 | L59 | S |
| 62 | L60 | N |
| 63 | L61 | R |
| 64 | L62 | F |
| 65 | L63 | S |
| 66 | L64 | G |
| 67 | L65 | S |
| 68 | L66 | K |
| 69 | L67 | S |
| 70 | L68 | G |
| 71 | L69 | N |
| 72 | L70 | T |
| 73 | L71 | A |
| 74 | L72 | S |
| 75 | L73 | L |
| 76 | L74 | T |
| 77 | L75 | I |
| 78 | L76 | S |
| 79 | L77 | G |
| 80 | L78 | L |
| 81 | L79 | Q |
| 82 | L80 | A |
| 83 | L81 | E |
| 84 | L82 | D |
| 85 | L83 | E |
| 86 | L84 | A |
| 87 | L85 | D |
| 88 | L86 | Y |
| 89 | L87 | Y |
| 90 | L88 | C |
| 91 | L89 | S |
| 92 | L90 | S |
| 93 | L91 | Y |
| 94 | L92 | T |
| 95 | L93 | Y |
| 96 | L94 | Y |
| 97 | L95 | S |
| 98 | L95A | T |
| 99 | L96 | R |
| 100 | L97 | V |
| 101 | L98 | F |
| 102 | L99 | G |
| 103 | L100 | G |
| 104 | L101 | G |
| 105 | L102 | T |
| 106 | L103 | K |
| 107 | L104 | L |
| 108 | L105 | A |
| 109 | L106 | V |
| 110 | L106A | L |
| 111 | L107 | G |

Accordingly, the L-CDR1 of C2 is defined by the sequence ranging from the amino acid residue at position 23 to the amino acid residue at position 36 in SEQ ID NO:2.

Accordingly, the L-CDR2 of C2 is defined by the sequence ranging from the amino acid residue at position 52 to the amino acid residue at position 58 in SEQ ID NO:2.

Accordingly, the L-CDR3 of C2 is defined by the sequence ranging from the amino acid residue at position 91 to the amino acid residue at position 100 in SEQ ID NO:2.

The present invention thus provides antibodies comprising functional variants of the VL region, VH region, or one or more CDRs of C2. A functional variant of a VL, VH, or CDR used in the context of a human monoclonal antibody of the present invention still allows the antibody to retain at least a substantial proportion (at least about 50%, 60%, 70%, 80%, 90%, 95% or more) of the affinity/avidity and/or the specificity/selectivity of the parent antibody (i.e. C2 antibody) and in some cases such a human monoclonal antibody of the present invention may be associated with greater affinity, selectivity and/or specificity than the parent Ab. Such functional variants typically retain significant sequence identity to the parent Ab. The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements. The sequences of CDR variants may differ from the sequence of the CDRs of the parent antibody sequences through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of C2. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 70% of identity to the parent peptide.

In some embodiments, the antibody of the present invention comprises 1, 2, 3, 4, 5, or 6 substitutions in the H-CDR1 of C2.

In some embodiments, the antibody of the present invention comprises 1, 2, 3, 4, 5, 6, 7, 8, 9, 10, 11, 12, 13, 14, 15 or 16 substitutions in the H-CDR2 of C2.

In some embodiments, the antibody of the present invention comprises 1, 2, 3, 4, 5, 6, 7, 8, 9, or 10 substitutions in the H-CDR3 of C2.

In some embodiments, the antibody of the present invention comprises 1, 2, 3, 4, 5, 6, 7, 8, 9, 10, 11, 12, or 13 substitutions in the L-CDR1 of C2.

In some embodiments, the antibody of the present invention comprises 1, 2, 3, 4, 5, or 6 substitutions in the L-CDR2 of C2.

In some embodiments, the antibody of the present invention comprises 1, 2, 3, 4, 5, 6, 7, 8, or 9 substitutions in the L-CDR3 of C2.

According to the present invention a first amino acid sequence having at least 50% of identity with a second amino acid sequence means that the first sequence has 50, 51, 52, 53, 54, 55, 56, 57, 58, 59, 60, 61, 62, 63, 64, 65, 66, 67, 68, 69, 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the present invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence.

In some embodiments, the human monoclonal antibody of the present invention is an antibody comprising a heavy chain comprising i) a H-CDR1 having at least 50% of identity with the H-CDR1 of C2, ii) a H-CDR2 having at least 50% of identity with the H-CDR2 of C2 and iii) a H-CDR3 having at least 50% of identity with the H-CDR3 of C2.

In some embodiments, the human monoclonal antibody of the present invention is an antibody comprising a light chain comprising i) a L-CDR1 having at least 50% of identity with the L-CDR1 of C2, ii) a L-CDR2 having at least 50% of identity with the L-CDR2 of C2 and iii) a L-CDR3 having at least 50% of identity with the L-CDR3 of C2.

In some embodiments, the human monoclonal antibody of the present invention is an antibody comprising a heavy chain comprising i) a H-CDR1 having at least 50% of identity with the H-CDR1 of C2, ii) a H-CDR2 having at least 50% of identity with the H-CDR2 of C2 and iii) a H-CDR3 having at least 50% of identity with the H-CDR3 of C2 and a light chain comprising i) a L-CDR1 having at least 50% of identity with the L-CDR1 of C2, ii) a L-CDR2 having at least 50% of identity with the L-CDR2 of C2 and iii) a L-CDR3 having at least 50% of identity with the L-CDR3 of C2.

In some embodiments, the human monoclonal antibody of the present invention is an antibody comprising a heavy chain comprising i) the H-CDR1 of C2, ii) the H-CDR2 of C2 and iii) the H-CDR3 of C2.

In some embodiments, the human monoclonal antibody of the present invention is an antibody comprising a light chain comprising i) the L-CDR1 of C2, ii) the L-CDR2 of C2 and iii) the L-CDR3 of C2.

In some embodiments, the human monoclonal antibody of the present invention is an antibody comprising a heavy chain comprising i) the H-CDR1 of C2, ii) the H-CDR2 of C2 and iii) the H-CDR3 of C2 and a light chain comprising i) the L-CDR1 of C2, ii) the L-CDR2 of C2 and iii) the L-CDR3 of C2.

In some embodiments, the human monoclonal antibody of the present invention is an antibody comprising a heavy chain having at least 70% of identity with SEQ ID NO:1.

In some embodiments, the human monoclonal antibody of the present invention is an antibody comprising a light chain having at least 70 of identity with SEQ ID NO:2.

In some embodiments, the human monoclonal antibody of the present invention is an antibody comprising a heavy chain having at least 70% of identity with SEQ ID NO:1 and a light chain having at least 70% of identity with SEQ ID NO:2.

In some embodiments, the human monoclonal antibody of the present invention is an antibody comprising a heavy chain which is identical to SEQ ID NO:1.

In some embodiments, the human monoclonal antibody of the present invention is an antibody comprising a light chain identical to SEQ ID NO:2.

In some embodiments, the human monoclonal antibody of the present invention is an antibody comprising a heavy chain identical to SEQ ID NO:1 and a light chain identical to SEQ ID NO:2.

The antibody of the present invention can be characterized by one or more of the functional or structural features of the aspects described above, or by any combination of selected functional and structural features.

The antibody of the present invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a human monoclonal antibody of the present invention may be switched by known methods. Typical, class switching techniques may be used to convert one IgG subclass to another, for instance from IgG1 to IgG2. Thus, the effector function of the human monoclonal antibodies of the present invention may be changed by isotype switching to, e.g., an IgG1, IgG2, IgG3, IgG4, IgD, IgA, IgE, or IgM antibody for various therapeutic uses. In some embodiments, the antibody of the present invention is a full-length antibody. In some embodiments, the full-length antibody is an IgG1 antibody. In some embodiments, the full-length antibody is an IgG4 antibody. In some embodiments, the OX1R-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys (SEQ ID NO:9) sequence. Other suitable stabilized IgG4 antibodies are disclosed in WO2008145142, which is hereby incorporated by reference in its entirety. In some embodiments, the human monoclonal antibody of the present invention is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

In addition or alternative to modifications made within the framework or CDR regions, antibodies of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, a human monoclonal antibody of the present invention may be chemically modified (e.g., one or more chemical moieties can be attached to the antibody) or be modified to alter its glycosylation, again to alter one or more functional properties of the antibody. For example, it will be appreciated that the affinity of antibodies provided by the present invention may be altered using any suitable method known in the art. The present invention therefore also relates to variants of the antibody molecules of the present invention, which have an improved affinity for OX1R. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In some embodiments, the hinge region of CHI is modified such that the number of cysteine residues in the hinge region is altered, e.g., increased or decreased. This approach is described further in U.S. Pat. No. 5,677,425 by Bodmer et al. The number of cysteine residues in the hinge region of CHI is altered to, for example, facilitate assembly of the light and heavy chains or to increase or decrease the stability of the antibody.

In some embodiments, the human monoclonal antibody of the present invention is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta et al.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by ldusogie et al.

In some embodiments, one or more amino acid residues are altered to thereby alter the ability of the antibody to fix complement. This approach is described further in PCT Publication WO 94/29351 by Bodmer et al. In some embodiments, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcyRI, FcyRII, FcyRIII and FcRn have been mapped and variants with improved binding have been described (see Shields, R. L. et al, 2001 J. Biol. Chen. 276:6591-6604, WO2010106180).

In some embodiments, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the human monoclonal antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (eurekainc.com/a&boutus/companyoverview.html). Alternatively, the human monoclonal antibodies of the present invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the present invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-poly ethylene glycol or polyethylene glycol-maleimide. In some embodiments, the antibody to be pegylated is an aglycosylated antibody. Methods for pegylating proteins are known in the art and can be applied to the human monoclonal antibodies of the present invention. See for example, EP 0 154 316 by Nishimura et al. and EP 0 401 384 by Ishikawa et al.

Another modification of the antibodies that is contemplated by the present invention is a conjugate or a protein fusion of at least the antigen-binding region of the human monoclonal antibody of the present invention to serum protein, such as human serum albumin or a fragment thereof to increase half-life of the resulting molecule. Such approach is for example described in Ballance et al. EP0322094.

In some embodiments, the antibody is an antigen-binding fragment. Antibody fragments can be obtained by conventional techniques, such as by fragmentation of full-length antibodies or by expression of nucleic acids encoding antibody fragments in recombinant cells (see, for instance Evans et al., J. Immunol. Meth. 184, 123-38 (1995)). The fragments can then be tested or screened for their properties in the same manner as described herein for full-length antibodies. The following describe exemplary formats for OX1R-specific antigen-binding fragments of the present invention:

F(ab')2 fragments, which are bivalent fragments comprising two Fab fragments linked by a disulfide bridge at the hinge region. These can be generated by, e.g., treating a full-length antibody with pepsin.

Fab' or Fab fragments, which are monovalent fragments consisting of the VL, VH, CL and CH1 domains. Fab fragments can be obtained, e.g., by treating an IgG antibody with papain. Fab' fragments can be obtained, e.g., by reducing the disulfide bridges of a F(ab')2 fragment using a reducing agent such as dithiothreitol.

Fd fragments, which consist essentially of the VH and CH1 domains.

Fv fragments, which consist essentially of the VL and VH domains of a single arm of an antibody and single-chain antibodies thereof. Single-chain antibodies (also known as single chain Fv (scFv) antibodies) are constructs where the VL and VH domains of an Fv fragment are joined, using recombinant methods, by a synthetic linker that enables them to be expressed as a single protein chain in which the VL and VH regions pair to form monovalent molecules (see for instance Bird et a/., Science 242, 423-426 (1988) and Huston et al., PNAS USA 85, 5879-5883 (1988)).

Fragments which comprise or consist of the VL or VH chains as well as amino acid sequence having at least 70% of identity with SEQ ID NO:1 or SEQ ID NO:2.

In some embodiments, the present invention provides a multispecific antibody comprising a first antigen binding site from a human monoclonal antibody of the present invention molecule described herein above and at least one second antigen binding site. In some embodiments, the second antigen-binding site is used for recruiting a killing mechanism such as, for example, by binding an antigen on a human effector cell or by binding a cytotoxic agent or a second therapeutic agent. As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radio labeled peptides), chemotherapeutic agents and prodrugs.

In some embodiments, the second antigen-binding site binds to an antigen on a human B cell, such as, e.g., CD19, CD20, CD21, CD22, CD23, CD80, CD138 and HLA-DR.

In some embodiments, the second antigen-binding site binds a tissue-specific antigen, promoting localization of the bispecific antibody to a specific tissue.

In some embodiments, the second antigen-binding site binds to an antigen located on the same type of cell as the OX1R-expressing cell, typically a tumor-associated antigen (TAA), but has a binding specificity different from that of the first antigen-binding site. Such multi- or bispecific antibodies can enhance the specificity of the tumor cell binding and/or engage multiple effector pathways. Exemplary TAAs include carcinoembryonic antigen (CEA), prostate specific antigen (PSA), RAGE (renal antigen), a-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, Marti, MelanA, MUM-1, MUM-2, MUM-3, HLA-B7, Ep-CAM or a cancer-associated integrin, such as α5β3 integrin. Alternatively, the second antigen-binding site binds to a different epitope of OX1R. The second antigen-binding site may alternatively bind an angiogenic factor or other cancer-associated growth factor, such as a vascular endothelial growth factor, a fibroblast growth factor, epidermal growth factor, angiogenin or a receptor of any of these, particularly receptors associated with cancer progression, such as HER receptor (EGFR, HER2, HER3 or HER4), c-MET or IGFR.

In some embodiments, the second antigen-binding site is from a second human monoclonal antibody of the present invention, such as a human monoclonal antibody of the present invention.

Exemplary formats for the multispecific antibody molecules of the present invention include, but are not limited to (i) two antibodies cross-linked by chemical heteroconjugation, one with a specificity to OX1R and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivaient bispecific binding protein consisting of two identical Fab fragments linked to a different Fab fragment; (ix) a so-called SCORPION® molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as TRIOMAB® (trifunctional hybrid antibodies)/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), BICLONIC® (bispecific human IgG antibodies, Merus) and DUOBODY® (bispecific human IgG1 antibodies, Genmab A/S) technologies.

In some embodiments, the bispecific antibody is obtained or obtainable via a controlled Fab-arm exchange, typically using DUOBODY® (bispecific human IgG1 antibodies) technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is a human monoclonal antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is a human monoclonal antibody of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fe-regions are of the IgG1 isotype.

In some embodiments, the first Fc region has an amino acid substitution at a position selected from the group consisting of: 366, 368, 370, 399, 405, 407 and 409, and the second Fc region has an amino acid substitution at a position selected from the group consisting of: 366, 368, 370, 399, 405, 407 and 409, and wherein the first and second Fc regions are not substituted in the same positions.

In some embodiments, the first Fc region has an amino acid substitution at position 405, and said second Fc region has an amino acid substitution at a position selected from the group consisting of: 366, 368, 370, 399, 407 and 409, optionally 409.

In some embodiments, the first Fc region has an amino acid substitution at position 409, and said second Fc region has an amino acid substitution at a position selected from the group consisting of: 366, 368, 370, 399, 405, and 407, optionally 405 or 368.

In some embodiments, both the first and second Fc regions are of the IgG1 isotype, with the first Fc region having a Leu at position 405, and the second Fc region having an Arg at position 409.

The human monoclonal antibody of the present invention may be produced by any technique known in the art, such as, without limitation, any chemical, biological, genetic or enzymatic technique, either alone or in combination. For example, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the present invention relates to a nucleic acid sequence encoding a human monoclonal antibody of the present invention. In some embodiments, the nucleic acid sequence encodes a heavy chain and/or a light chain of a human monoclonal antibody of the present invention.

Typically, said nucleic acid is a DNA or RNA molecule, which may be included in any suitable vector. The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication-defective retroviruses, adenoviruses and adeno-associated viruses), which serve equivalent functions.

So, a further object of the present invention relates to a vector comprising a nucleic acid of the present invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a host cell which has been transfected, infected or transformed by a nucleic acid and/or a vector according to the present invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the present invention may be used to produce a human monoclonal antibody of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculo virus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofo late reductase gene (hereinafter referred to as "DHFR gene") is defective (Urlaub G et al; 1980), rat YB2/3HL.P2.G1 1.16Ag.20 cell (ATCC CRL1662, hereinafter referred to as "YB2/0 cell"), and the like.

The present invention also relates to a method of producing a recombinant host cell expressing an antibody according to the present invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

In another aspect, the present invention relates to the human monoclonal antibody of the present invention, as defined in any aspect or embodiment herein, for use as a medicament.

In another aspect, the present invention relates to a method of treating cancer in a subject in need thereof comprising administering the subject with a therapeutically effective amount of a human monoclonal antibody of the present invention.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the present invention contemplate any one or more of these aspects of treatment.

Typically, the cancer may be selected from the group consisting of bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating, lobular carcinoma, lobular carcinoma in, situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinroma, clear cell), esophagus cancer, gallbladder cancer (mucinous adenocarcinoma, small cell carcinoma), gastrointestinal carcinoid tumors (e.g. choriocarcinoma, chorioadenoma *destruens*), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyo sarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In some embodiments, the subject suffers from an epithelial cancer. As used herein, the term "epithelial cancer" refers to any malignant process that has an epithelial origin. Examples of epithelial cancers include, but are not limited to, a gynecological cancer such as endometrial cancer, ovarian cancer, cervical cancer, vulvar cancer, uterine cancer or fallopian tube cancer, breast cancer, prostate cancer, lung cancer, pancreatic cancer, urinary cancer, bladder cancer, head and neck cancer, oral cancer colorectal cancer and liver cancer. An epithelial cancer may be at different stages as well as varying degrees of grading. In some embodiments, the epithelial cancer is selected from the group consisting of breast cancer, prostate cancer, lung cancer, pancreatic cancer, bladder cancer colorectal cancer and ovarian cancer. In some embodiments, the epithelial cancer is a colorectal cancer. In some embodiments, the epithelial cancer is a liver cancer, in particular a hepatocellular carcinoma. In some embodiments, the epithelial cancer is breast cancer. In some embodiments, the epithelial cancer is ovarian cancer. In some embodiments, the epithelial cancer is prostate cancer, in particular advanced prostate cancer. In some embodiments, the epithelial cancer is lung cancer. In some embodiments, the epithelial cancer is head and neck cancer. In some embodiments, the epithelial cancer is head and neck squamous cell carcinoma.

As used herein the term "pancreatic cancer" or "pancreas cancer" as used herein relates to cancer which is derived from pancreatic cells. In particular, pancreatic cancer included pancreatic adenocarcinoma (e.g., pancreatic ductal adenocarcinoma) as well as other tumors of the exocrine pancreas (e.g., serous cystadenomas), acinar cell cancers, intraductal papillary mucinous neoplasms (IPMN) and pancreatic neuroendocrine tumors (such as insulinomas).

As used herein the term "hepatocellular carcinoma" has its general meaning in the art and refers to the cancer developed in hepatocytes. In general, liver cancer indicates hepatocellular carcinoma in large. HCC may be caused by an infectious agent such as hepatitis B virus (HBV, hereinafter may be referred to as HBV) or hepatitis C virus (HCV, hereinafter may be referred to as HCV). In some embodiments, HCC results from alcoholic steatohepatitis or non-alcoholic steatohepatitis (hereinafter may be abbreviated to as "NASH"). In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC.

As used herein the term "advanced prostate cancer" has its general meaning in the art. "Castration resistant prostate cancer", "CaP", "androgen-receptor dependent prostate cancer", "androgen-independent prostate cancer", are used interchangeably to refer to prostate cancer in which prostate cancer cells "grow" {i.e., increase in number) in the absence of androgens and/or in the absence of expression of androgen receptors on the cancer cells.

As used herein, the term "therapeutically effective amount" refers to an amount effective, at dosages and for periods of time necessary, to achieve a desired therapeutic result. A therapeutically effective amount of a human monoclonal antibody of the present invention may vary according to factors such as the disease state, age, sex, and weight of the individual, and the ability of the human monoclonal antibody of the present invention to elicit a desired response in the individual. A therapeutically effective amount is also one in which any toxic or detrimental effects of the antibody or antibody portion are outweighed by the therapeutically beneficial effects. The efficient dosages and dosage regimens for the human monoclonal antibody of the present invention depend on the disease or condition to be treated and may be determined by the persons skilled in the art. A physician having ordinary skill in the art may readily determine and prescribe the effective amount of the pharmaceutical composition required. For example, the physician could start doses of the human monoclonal antibody of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the compound to inhibit cell growth or to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of a human monoclonal antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of a human monoclonal antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by measuring the level of OX1R in a sample containing tumor cells, by visualization of the disease area, or by other diagnostic methods described further herein, e.g. by performing one or more PET-CT scans, for example using a labeled human monoclonal antibody of the present invention, fragment or mini-antibody derived from the human monoclonal antibody of the present invention. If desired, an effective daily dose of a pharmaceutical composition may be administered as two, three, four, five, six or more sub-doses administered separately at appropriate intervals throughout the day, optionally, in unit dosage forms. In some embodiments, the human monoclonal antibodies of the present invention are administered by slow continuous infusion over a long period, such as more than 24 hours, in order to minimize any unwanted side effects. An effective dose of a human monoclonal antibody of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of a compound of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

The present invention also provides for therapeutic applications where a human monoclonal antibody of the present invention is used in combination with at least one further therapeutic agent for treating cancer. Such administration may be simultaneous, separate or sequential. For simultaneous administration the agents may be administered as one composition or as separate compositions, as appropriate.

The further therapeutic agent is typically relevant for the disorder to be treated. Exemplary therapeutic agents include other anti-cancer antibodies, cytotoxic agents, chemotherapeutic agents, anti-angiogenic agents, anti-cancer immunogens, cell cycle control/apoptosis regulating agents, hormonal regulating agents, and other agents described below.

In one aspect, the further therapeutic agent is at least one second antibody which binds another target such as, e.g., CC2, CD5, CD8, CD14, CD15, CD19, CD21, CD22, CD23, CD25, CD30, CD33, CD37, CD38, CC20, CC20L, CC26, CD52, CD54, CD80, CD126, B7, MUC1, tenascin, HM 1.24, or HLA-DR. For example, the second antibody may bind to a B cell antigen, including, but not limited to CD20, CD19, CD21, CD23, CD38, CC26, CD80, CD138, HLA-DR, CD22, or to another epitope on OX1R. In some embodiments, the second antibody binds vascular endothelial growth factor A (VEGF-A). In some embodiments, the human monoclonal antibody of the present invention is for use in combination with a specific therapeutic antibody. Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Other examples include anti-CTLA4 antibodies (e.g. Ipilimumab), anti-PD1 antibodies, anti-PDL1 antibodies, anti-TIMP3 antibodies, anti-LAG3 antibodies, anti-B7H3 antibodies, anti-B7H4 antibodies or anti-B7H6 antibodies. In some embodiments, antibodies include B cell depleting antibodies. Typical B cell depleting antibodies include but are not limited to anti-CD20 monoclonal antibodies [e.g. Rituximab (Roche), Ibritumomab tiuxetan (Bayer Schering), Tositumomab (GlaxoSmithKline), AME-133v (Applied Molecular Evolution), Ocrelizumab (Roche), Ofatumumab (HuMax-CD20, Gemnab), TRU-015 (Trubion) and IMMU-106 (Immunomedics)], an anti-CD22 antibody [e.g. Epratuzumab, Leonard et al., Clinical Cancer Research (Z004) 10: 53Z7-5334], anti-CD79a antibodies, anti-CD27 antibodies, or anti-CD19 antibodies (e.g. U.S. Pat. No. 7,109,304), anti-BAFF-R antibodies (e.g. Belimumab, GlaxoSmithKline), anti-APRIL antibodies (e.g. anti-human APRIL antibody, ProSci inc.), and anti-IL-6 antibodies [e.g. previously described by De Benedetti et al., J Immunol (2001) 166: 4334-4340 and by Suzuki et al., Europ J of Immunol (1992) 22 (8) 1989-1993, fully incorporated herein by reference].

In some embodiments, the human monoclonal antibody of the present invention is used in combination with a chemotherapeutic agent. The term "chemotherapeutic agent" refers to chemical compounds that are effective in inhibiting tumor growth. Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; amino levulinic acid; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK® (polysaccharide K); (razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and phannaceutically acceptable salts, acids or derivatives of any of the above. Also included in this definition are antihorrnonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and phannaceutically acceptable salts, acids or derivatives of any of the above.

In some embodiments, the human monoclonal antibody of the present invention is used in combination with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (IRESSA®), sunitinib (SUTENT®; SU11248), erlotinib (TARCEVA®; OSI-1774), lapatinib (GW572016; GW2016), canertinib (CI 1033), semaxinib (SU5416), vatalanib (PTK787/ZK222584), sorafenib (BAY 43-9006), imatinib (GLEEVEC®; STI571), leflunomide (SU101), vandetanib (ZACTIMA®; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100, 254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In some embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the human monoclonal antibody of the present invention is used in combination with a HER inhibitor. In some embodiments, the HER inhibitor is an EGFR inhibitor. GFR inhibitors are well known in the art (Inhibitors of erbB-1 kinase; Expert Opinion on Therapeutic Patents December 2002, Vol. 12, No. 12, Pages 1903-1907, Susan E Kane. Cancer therapies targeted to the epidermal growth factor receptor and its family members. Expert Opinion on Therapeutic Patents February 2006, Vol. 16, No. 2, Pages 147-164. Peter TrOX1Rer Tyrosine kinase inhibitors in cancer treatment (Part II). Expert Opinion on Therapeutic Patents December 1998, Vol. 8, No. 12, Pages 1599-1625). Examples of such agents include antibodies and small organic molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). Examples of small organic molecules that bind to EGFR include ZD1839 or Gefitinib (IRESSA™; Astra Zeneca); CP-358774 or erlotinib (TARCEVA™; Genentech/OSI); and AG1478, AG1571 (SU 5271; Sugen); EMD-7200. In some embodiments, the HER inhibitor is a small organic molecule pan-HER inhibitor such as dacomitinib (PF-00299804). In some embodiments, the HER inhibitor is selected from the group consisting of cetuximab, panitumumab, zalutumumab, nimotuzumab, erlotinib, gefitinib, lapatinib, neratinib, canertinib, vandetanib, afatinib, TAK-285 (dual HER2 and EGFR inhibitor), ARRY334543 (dual HER2 and EGFR inhibitor), Dacomitinib (pan-ErbB inhibitor), OSI-420 (Desmethyl Erlotinib) (EGFR inhibitor), AZD8931 (EGFR, HER2 and HER3 inhibitor), AEE788 (NVP-AEE788) (EGFR, HER2 and VEGFR 1/2 inhibitor), Pelitinib (EKB-569) (pan-ErbB inhibitor), CUDC-101 (EGFR, HER2 and HDAC inhibitor), XL647 (dual HER2 and EGFR inhibitor), BMS-599626 (AC480) (dual HER2 and EGFR inhibitor), PKC412 (EGFR, PKC, cyclic AMP-dependent protein kinase and S6 kinase inhibitor), BIBX1382 (EGFR inhibitor) and AP261 13 (ALK and EGFR inhibitor). The inhibitors cetuximab, panitumumab, zalutumumab, nimotuzumab are monoclonal antibodies. erlotinib, gefitinib, lapatinib, neratinib, canertinib, vandetanib and afatinib are tyrosine kinase inhibitors.

In some embodiments, the human monoclonal antibody of the present invention is used in combination with a c-Met inhibitor. In some embodiments the c-Met inhibitor is an anti-c-Met antibody. In some embodiments, the anti-c-met antibody is METMAB® (onartuzumab) or a biosimilar version thereof. METMAB® (onartuzumab) is disclosed in, for example, WO2006/015371; Jin et al, Cancer Res (2008) 68:4360. Other anti-c-met antibodies suitable for use in the methods of the present invention are described herein and known in the art. For example, anti-c-met antibodies disclosed in WO05/016382 (including but not limited to antibodies 13.3.2, 9.1.2, 8.70.2, 8.90.3); an anti-c-met antibodies produced by the hybridoma cell line deposited with ICLC number PD 03001 at the CBA in Genoa, or that recognizes an epitope on the extracellular domain of the β chain of the HGF receptor, and said epitope is the same as that recognized by the monoclonal antibody); anti-c-met antibodies disclosed in WO2007/126799 (including but not limited to 04536, 05087, 05088, 05091, 05092, 04687, 05097, 05098, 05100, 05101, 04541, 05093, 05094, 04537, 05102, 05105, 04696, 04682); anti c-met antibodies disclosed in WO2009/007427 (including but not limited to an antibody deposited at CNCM, Institut Pasteur, Paris, France, on Mar. 14, 2007 under the number 1-3731, on Mar. 14, 2007 under the number 1-3732, on Jul. 6, 2007 under the number 1-3786, on Mar. 14, 2007 under the number 1-3724; an anti-c-met antibody disclosed in 20110129481; an anti-c-met antibody disclosed in US20110104176; an anti-c-met antibody disclosed in WO2009/134776; an anti-c-met antibody disclosed in WO2010/059654; an anti-c-met antibody disclosed in WO2011020925 (including but not limited to an antibody secreted from a hybridoma deposited at the CNCM, Institut Pasteur, Paris, France, on Mar. 12, 2008 under the number 1-3949 and the hybridoma deposited on Jan. 14, 2010 under the number 1-4273). In some embodiments, the cMET inhibitor is selected from the group consisting of K-252a; SU-11274; PHA-665752 and other cMET inhibitors described in WO 2002/096361; AM7; AMG-208 and other cMet inhibitors described in WO 2009/091374; JNJ-38877605 and other cMet inhibitors described in WO 2007/075567; MK-2461 and other cMet inhibitors described in WO 2007/002254 and/or WO 2007/002258; PF-04217903 and other cMet inhibitors described in WO 2007/132308; BMS 777607; GSK 136089 (also known as XL-880 and Foretinib) and other cMET inhibitors described in WO 2005/030140; BMS 907351 (also known as XL-184); EMD 1214063; LY 2801653; ARQ 197; MK 8033; PF 2341066 and other cMET inhibitors described in WO 2006/021881; MGCD 265; E 7050; MP 470; SGX 523; cMet inhibitors described in Kirin J. J. Cui, Inhibitors targeting hepatocyte growth factor receptor and their potential therapeutic applications. Expert Opin. Ther. Patents 2007; 17: 1035-45; cMet inhibitors described in WO 2008/103277; cMet inhibitors described in WO 2008/008310; cMet inhibitors described in WO 2007/138472; cMet inhibitors described in WO 2008/008539; cMet inhibitors described in WO 2009/007390; cMet inhibitors described in WO 2009/053737; cMet inhibitors described in WO 2009/024825; cMet inhibitors described in WO 2008/071451; cMet inhibitors described in WO 2007/130468; cMet inhibitors described in WO 2008/051547; cMet inhibitors described in WO 2008/053157; cMet inhibitors described in WO 2008/017361; WO 2008/145242; WO2008/145243; WO 2008/148449; WO 2009/007074; WO 2009/006959; WO 2009/024221; WO 2009/030333; and/or WO 2009/083076; cMet inhibitors described in WO 2009/093049; cMet inhibitors described in US 2008/039457; cMet inhibitors described in WO 2007/149427; cMet inhibitors described in WO 2007/050309; cMet inhibitors described in WO 2009/056692; cMet inhibitors described in WO 2009/087305; cMet inhibitors described in US 2009/197864; cMet inhibitors described in US 2009/197862; cMet inhibitors described in US 2009/156594; cMet inhibitors described in WO 2008/124849; cMet inhibitors described in WO 2008/067119; cMet inhibitors described in WO 2007/064797; cMet inhibitors described in WO 2009/045992; cMet inhibitors described in WO 2008/088881; cMet inhibitors described in WO 2007/081978; cMet inhibitors described in WO 2008/079294; cMet inhibitors described in WO 2008/079291; cMet inhibitors described in WO 2008/086014; cMet inhibitors described in WO 2009/033084; cMet inhibitors described in WO 2007/059202; cMet inhibitors described in US 2009/170896; cMet inhibitors described in WO 2009/077874 and/or WO 2007/023768; cMet inhibitors described in WO 2008/049855; cMet inhibitors described in WO 2009/026717; and cMet inhibitors described in WO 2008/046216.

In some embodiments, the human monoclonal antibody of the present invention is used in combination with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-$\alpha$), IFN-beta (IFN-$\beta$) and IFN-gamma (IFN-$\gamma$). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include PROLEUKIN® (IL-2; Chiron Corporation) and NEUMEGA® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, NEUPOGEN® (G-CSF; Amgen), NEULASTA® (pelfilgrastim; Amgen), LEUKINE® (GM-CSF; Berlex), PROCRIT® (erythropoietin; Ortho Biotech), EPOGEN® (erythropoietin; Amgen), ARNESP® (erytropoietin).

Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILS), such as CC2+ and/or CD8+ T cells (for instance T cells expanded with tumor-specific antigens and/or genetic enhancements), antibody-expressing B cells or other antibody-producing or -presenting cells, dendritic cells (e.g., dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include CANVAXIN™, APC-8015 (Dendreon), HSPPC-96 (Antigenics), and MELACINE® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In some embodiments, the human monoclonal antibody of the present invention is used in combination with radiotherapy. Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium- 137, iridium-192, americium-241, gold-198, cobalt-57, copper-67, technetium-99, iodide-123, iodide-131, and indium-111.

For administration, the human monoclonal antibody of the present invention is formulated as a pharmaceutical composition. A pharmaceutical composition comprising a human monoclonal antibody of the present invention can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the present invention can be formulated for a topical, oral, parenteral, intranasal, intravenous, intramuscular, subcutaneous or intraocular administration and the like.

Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the human monoclonal antibody of the present invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A human monoclonal antibody of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The human monoclonal antibodies of the present invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In some embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospho lipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The present invention will be further illustrated by the following Figures and examples. However, these examples and Figures should not be interpreted in any way as limiting the scope of the present invention.

FIGURES

FIG. 1: Effect of OxB and anti-OX1R antibodies including B4, B10, C1, C2, D4, E7, H7 on the cell growth of HEK-OX1R cells expressing recombinant OX1R. Cells were treated for 48 h with 0.1 μM of each compound and then cells were counted. Results were expressed as the percentage of untreated cell number (Control).

Figure 2:
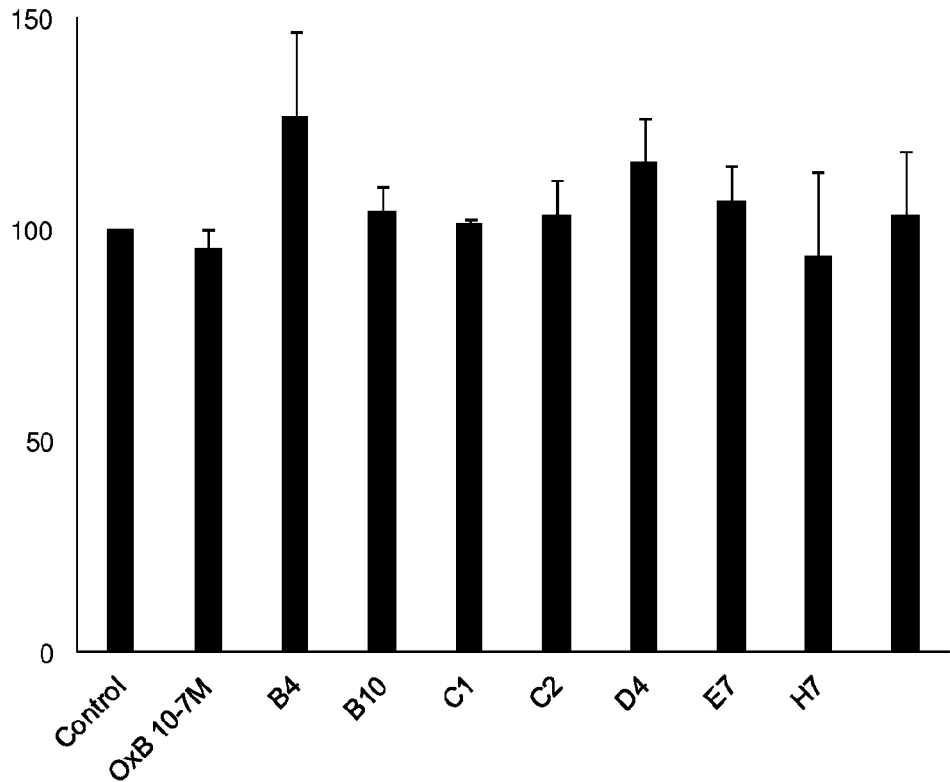

FIG. 2: Effect of OxB and anti-OX1R antibodies including B4, B10, C1, C2, D4, E7, 117 on the cell growth of HEK cells which do not express OX1R. Cells were treated for 48 h with 0.1 μM of each compound and then cells were counted. Results were expressed as the percentage of untreated cell number (Control).

Figure 3:
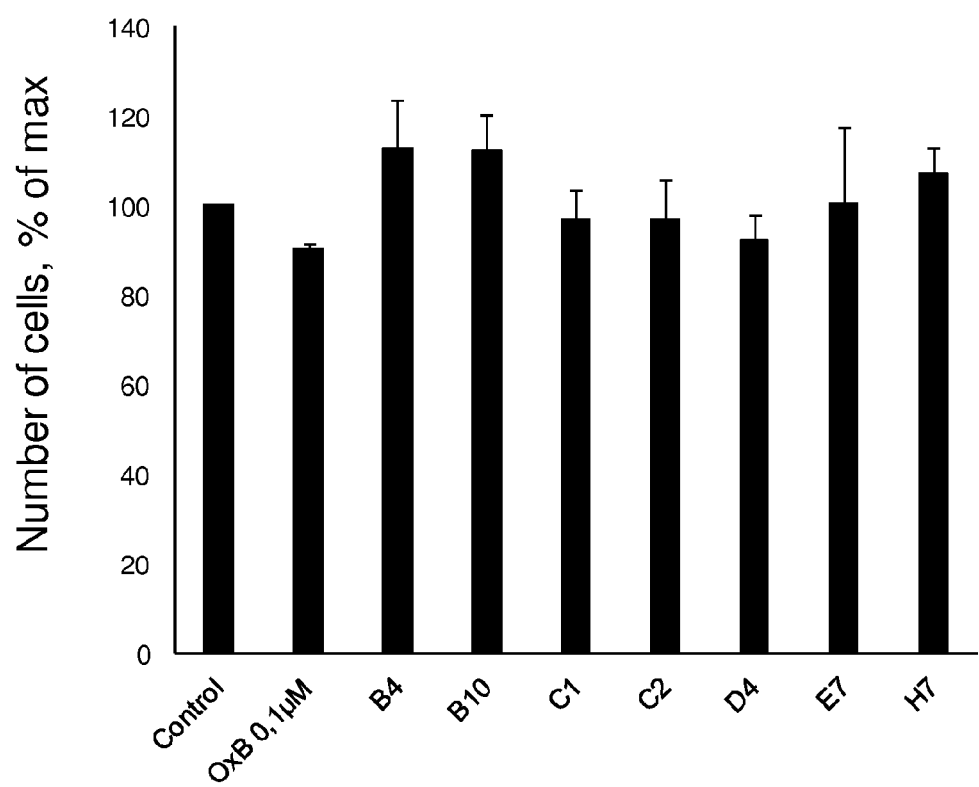

FIG. 3: Effect of OxB and anti-OX1R antibodies including B4, B10, C1, C2, D4, E7, H7 on the cell growth of HEK-OX1R in the presence of NSC87877. SHP-2 protein tyrosine phosphatase inhibitor, NSC-87877, blocks orexin-induced apoptosis. Cells were treated for 48 h with 0.104 of each compound and then cells were counted. Results were expressed as the percentage of untreated cell number (Control).

Figure 4:
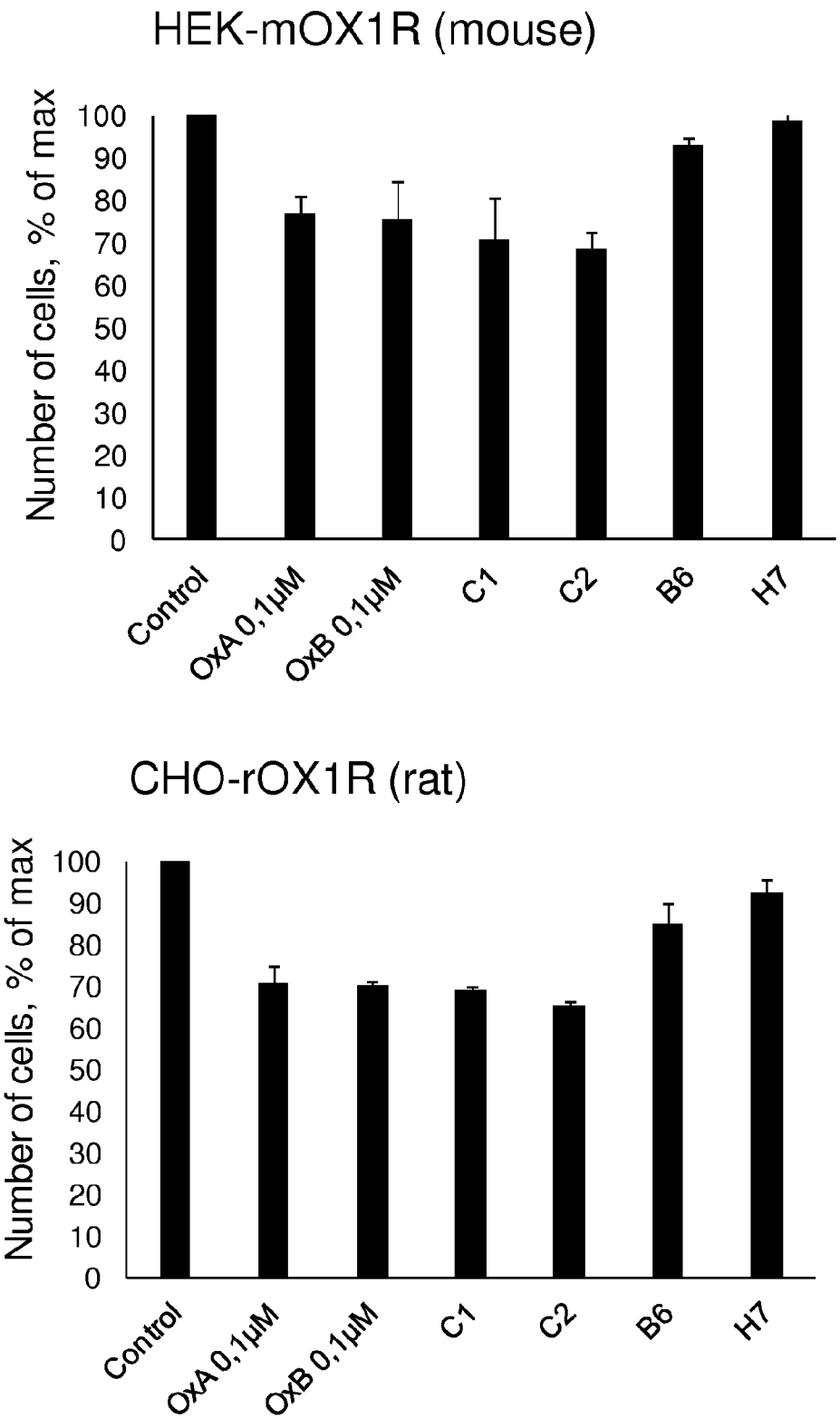

FIG. 4: Effect of OxB, OxA and anti-OX1R antibodies including C1, C2, B6, H7 on the cell growth of HEK-mouseOX1R (left) and CHO-ratOX1R. Cells were treated for 48 h with 0.1 μM of each compound and then cells were counted. Results were expressed as the percentage of untreated cell number (Control).

Figure 5A:
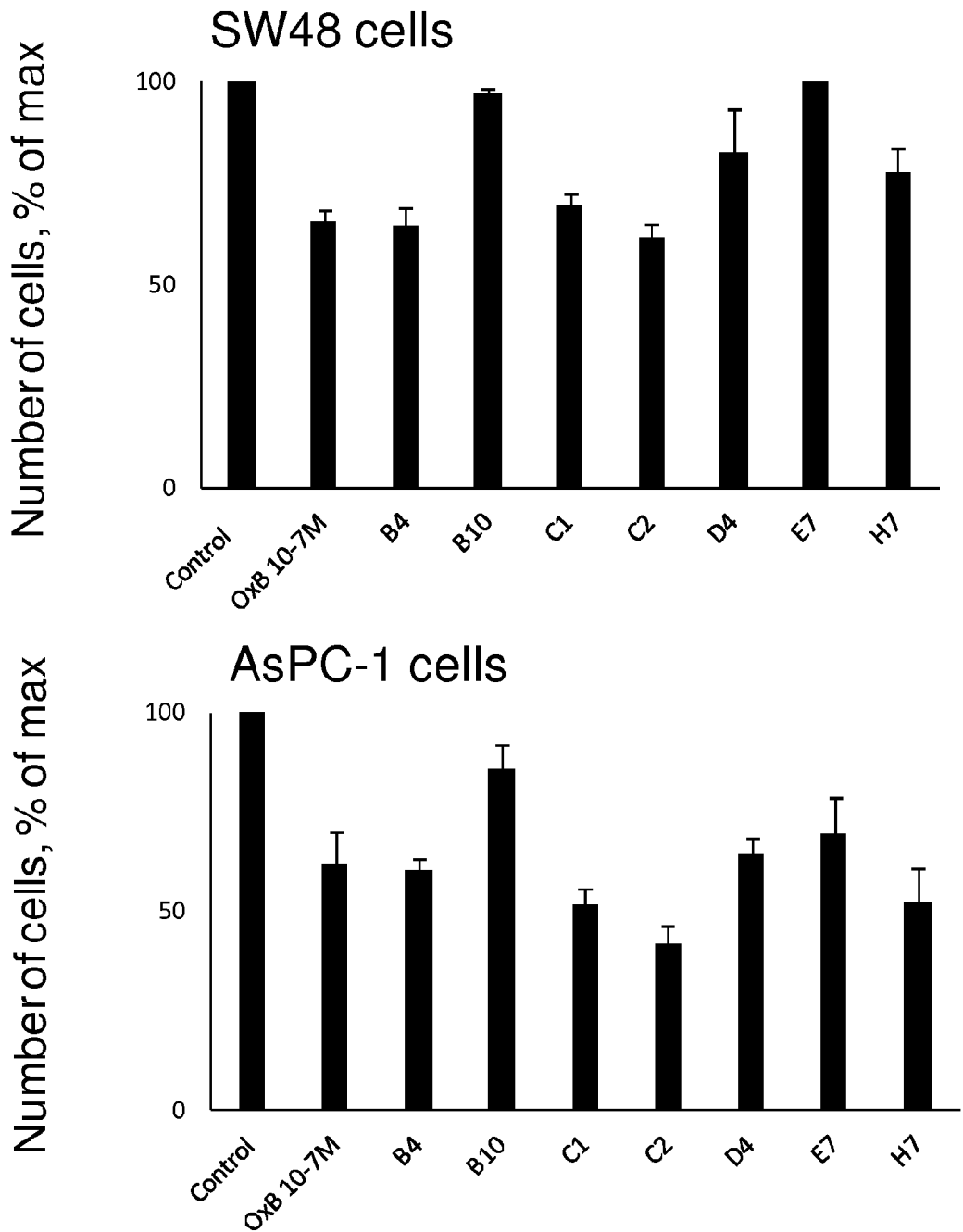
Figure 5B:
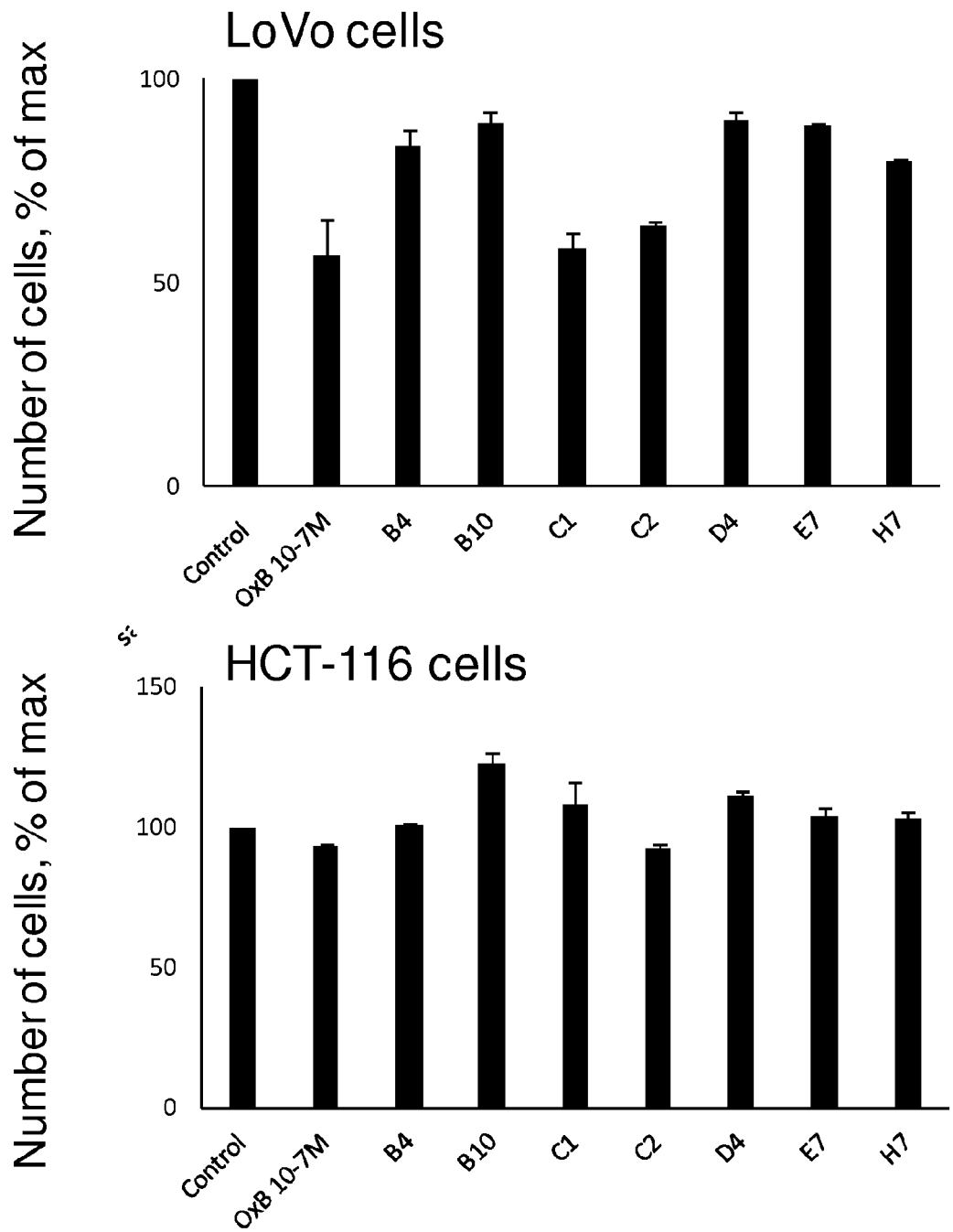

FIG. 5: Effect of OxB and anti-OX1R antibodies including B4, B10, C1, C2, D4, E7, H7 on the cell growth of colon cancer cells lines SW48 (top left) and LoVo (top right) which express OX1R; colon cancer cell line HCT-116 (bottom right) which does not expressed OX1R; and pancreas cancer cell line AsPC-1 (bottom left) which expressed OX1R. Cells were treated for 48 h with 0.1 μM of each compound and then cells were counted. Results were expressed as the percentage of untreated cell number (Control).

Figure 6:
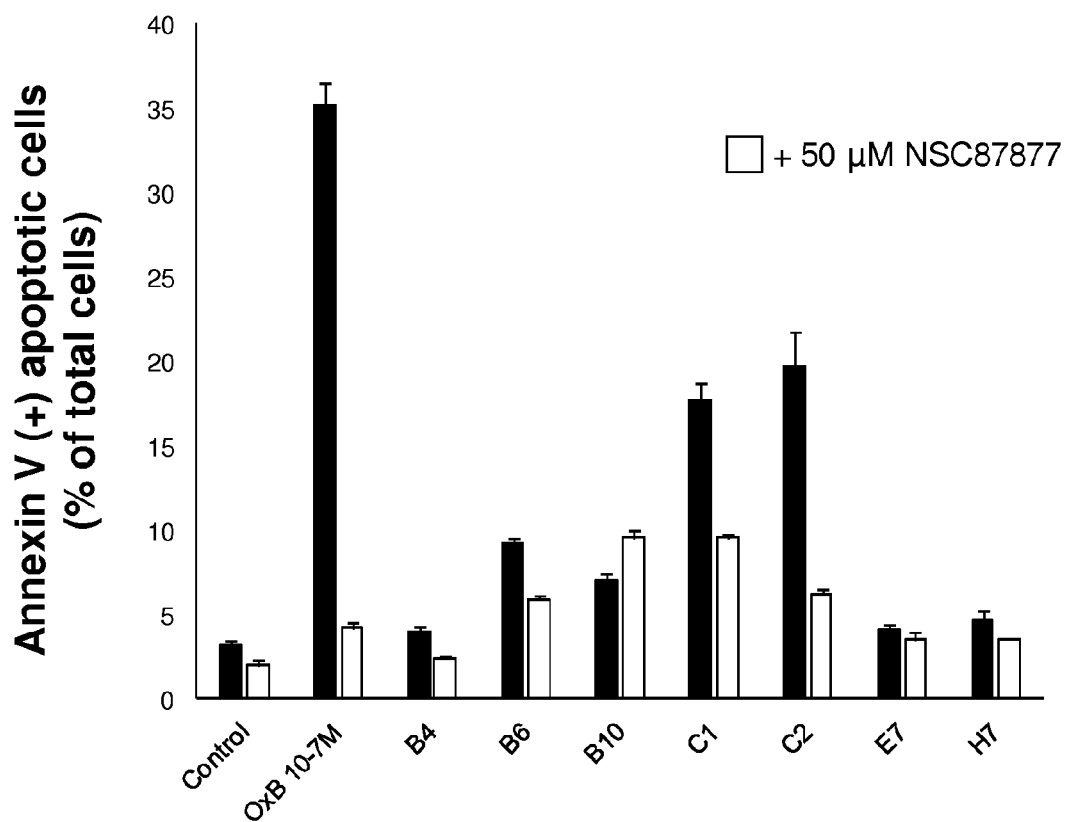

FIG. 6: Effect of OxB and anti-OX1R antibodies including B4, B6, B10, C1, C2, E7, and H7 on apoptosis in HEK-OX1R cells expressing recombinant OX1R. SHP-2 protein tyrosine phosphatase inhibitor, NSC-87877, blocks orexin-induced apoptosis. HEK-OX1R cells were challenged with 0.1 μM of each compound for 48 hr in the absence (black bars) or the presence (white bars) of NSC-87877 (50 μM). Apoptosis was measured by determination of annexin V-PE binding, and results are expressed as the percentage of apoptotic cells.

Figure 7:
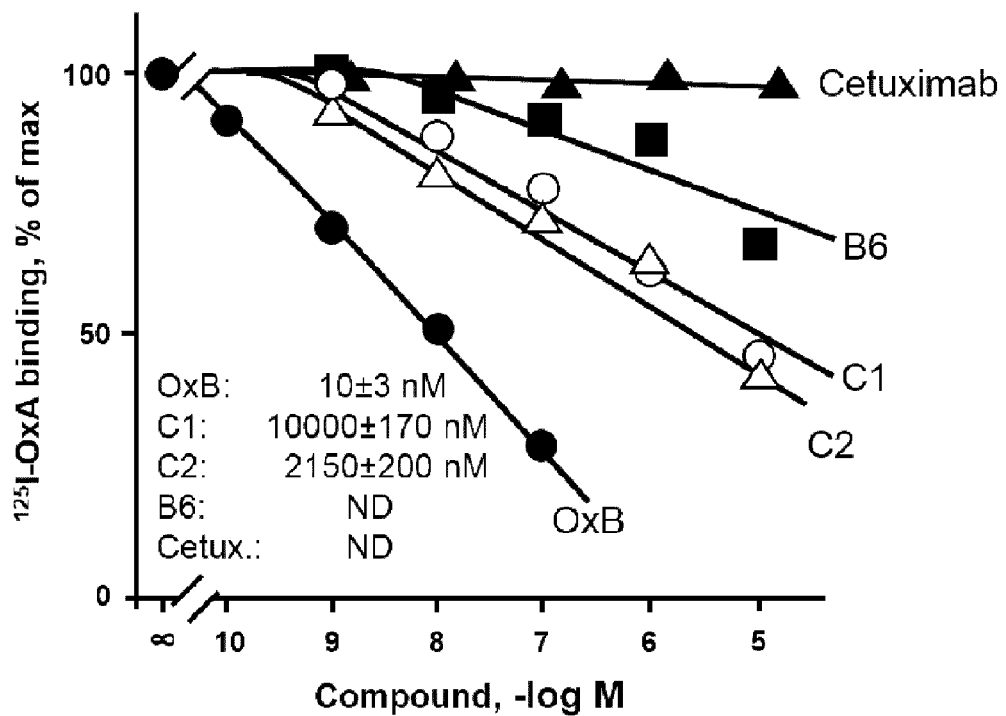

FIG. 7: Competitive inhibition of specific $^{125}$I-OxA binding to HEK-OX1R cells by increasing concentrations of unlabeled OxB, Cetuximab (irrelevant antibody) and anti-OX1R antibodies including B6, C1 and C2. Cells were incubated with the indicated concentration of OxB (●), Cetuximab (▲), B6 (■), C1 (○) and C2 (△). Results were expressed as the percentage of radioactivity specifically bound in the absence of added unlabeled compound. Each point is the mean of three separate experiments. ND, not determined.

Figure 8:
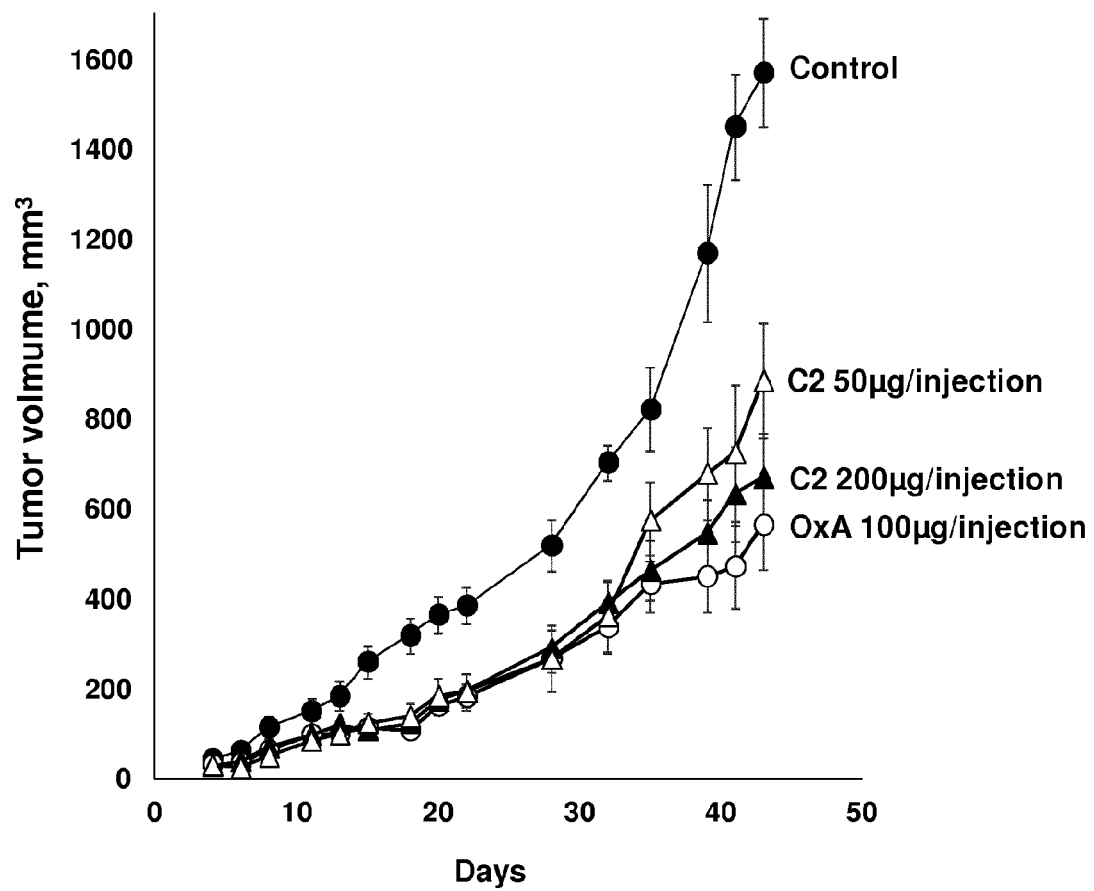

FIG. 8: Effect of inoculation of orexin-A and C2 antibody on the growth of tumors developed by xenografted human HT-29 cells in nude mice. Colon adenocarcinoma derived cells, HT-29, were inoculated in the flank of nude mice at day 0. Mice were injected at day 1 (2 injections/week) intraperitoneally with 100 μl of orexin-A solution (1.4 μmoles of orexin-A/Kg (white circles)) or with 100 μl of C2 antibody solution (0.065 μmoles/Kg (black triangles) or 0.02 μmoles/Kg (white triangles)) or with 100 μl of PBS (black circles) for control.

EXAMPLES

Example 1

The development of antibodies directed against OX1R were produced by a phage display strategy and the antibody selection was performed by using HEK and HEK stably expressing OX1R (HEK-OX1R) cell lines. As a first step, a batch of 7 different antibodies named B4, B10, C1, C2, D4, E7 and H7 was tested for their ability to inhibit the cell growth of HEK-OX1R. Cells were incubated with 0.1 μM of OxB or antibodies for 48 h in culture medium and then cells were counted in order to estimate the cellular growth. As shown in FIG. 1, C1 and C2 reduced the HEK-OX1R cell number of about 46%±3 and 37±3% respectively as compared to orexin-B (OxB, 0.1 μM) which reduced of 40±3% the cell number (FIG. 1). In contrast, B4, B10, D4, E7 and H7 have a weak effect on cellular growth (range from 14% to 20%) as compared to OxB (FIG. 1). To determine the specificity of the cellular growth inhibition induced by these antibodies, we test it on HEK cells which does not expressing OX1R. As shown in FIG. 2 no anti-OX1R antibodies induced a cellular growth inhibition demonstrating that the observed effects of C1, C2 and, to a lesser extent for B4, B10, D4, E7 and H7 on HEK-OX1R cellular growth were clearly associated to the presence of OX1R. As previously described orexins (A & B) induced a mitochondrial apoptosis mediated by an entirely novel mechanism, not related to Gq-mediated phospholipase C activation. In fact, orexins induced the tyrosine phosphorylation of two immunoreceptor tyrosine-based inhibitory motifs (ITIMs) located in the OX1R sequence. The resulting phosphorylated receptor could then recruit and activate the phosphotyrosine phosphatase, SHP-2, which is responsible for mitochondrial apoptosis, involving cytochrome c release from mitochondria to cytosol and caspase-3 and caspase-7 activation. Here, we tested the effect of SHP inhibitor (NSC 87877) on the ability of anti-OX1R to inhibit the cellular growth of HEK-OX1R (FIG. 3). HEK-OX1R cells were incubated 48 h with 0.1 µM of OxB or antibodies in the presence of 50 µM NSC 87877. As shown in FIG. 3, the inhibition of cellular growth induced by OxB (FIG. 1) was totally reverted in the presence of SHP inhibitor as compared to untreated cells, indicating that the orexin effect was well related to the recruitment of SHP2. Similarly, the inhibition of cellular growth induced by C1 and C2 but also by other antibodies (B4, B10, D4, E7 and H7) was totally reversed by NSC 87877. These results demonstrate that the cellular growth inhibition mediated by C1 and C2 was associated to the SHP2 signaling pathway as previously described for orexins/OX1R. Finally, we show that the antibodies are able to cross react between interspecies (human, rat and mouse), since the antibodies C1 and C2 are able to promote apotosis of CHO cells lines transfected with OX1R of mouse or rat (FIG. 4).

We have tested the ability of antibodies to inhibit the cellular growth in cancer cell lines derived from colon cancer (SW48, LoVo and HCT-116 cells) and pancreas cancer (AsPC-1 cells). Data reveal that: 1) C1, C2 and also B4 inhibit the cell growth in SW48 cells similarly to OxB (FIG. 5). D4 and H7 have a weak effect. In contrast, B10 and E7 have no effect on cell growth (FIG. 5). Moreover, all observed effects induced by antibodies were totally reversed in the presence of NSC 87877 inhibitor (not shown); 2) C1 and C2 inhibit the cell growth in LoVo cells similarly to OxB (FIG. 5). Inversely, B4, B10, D4, E7 and H7 have no or weak effect on cell growth; 3) all antibodies except B10 and E7 inhibit the cell growth in AsPC-1 cells derived from pancreas cancer. It should be noted that C1, C2 and B4 display a cell growth inhibition similar to OxB effect (FIG. 5); 4) all antibodies have no effect on cell growth of HCT-116 cells (FIG. 5) which do not express OX1R confirming that in the absence of orexin receptor, antibodies have no effect on cell growth of cancer cell lines. As previously described (see above) orexins are able to induce a mitochondrial apoptosis in cancer cell lines. We test the ability of antibodies to induce apoptosis in HEK-OX1R cells and colonic cancer cell line LoVo. Cells were incubated for 48 h in the presence of 0.1 µM OxB or 0.1 µM of each antibody and then, apoptosis was determined using the Guava PCA system and the Guava nexin kit. FIG. 6 shows that C1 and C2 are able to induce apoptosis in HEK-OX1R cells, respectively, 12±1% and 16±2% of total cells as compared to OxB, 37±2%. This effect was dose-dependent. Indeed when HEK-OX1R cells were treated with 0.01 µM of C2 antibody, cell apoptosis was only of 6±0.7% of total cells. In contrast, B4, E7 and H7 have no effect on cell apoptosis. It should be noted that B10 antibody has a weak effect on the induction of apoptosis but independent of the doses suggesting a non-specific response. In the same way, C2 antibody (0.1 µM) was able to induce apoptosis in LoVo cancer cell line. This apoptotic effect was dose dependent since the treatment of LoVo with 0.01 µM of C2 strongly reduce the apoptotic response. Taken together these results demonstrate that C2 and C1 are able 1) to induce a strong inhibition of cell growth and; 2) to stimulate the apoptosis in HEK-OX1R and cancer cell lines. These properties are specific since in the absence of OX1R expression (HEK and HCT-116 cells) or in the presence of SHP inhibitor (NSC 87877) these effects are totally abolished.

The ability of C1 and C2 antibodies to interact with the OX1R binding site was determined by competitive inhibition of $^{125}$I-OxA binding study. HEK-OX1R cells were incubated with $^{125}$I-OxA in the presence of increasing concentration of native OxB, C1 or C2 antibody and the resulting $^{125}$I-OxA specific binding was measured. As shown in FIG. 8, C1 and C2 antibodies were able to competitively inhibit the binding of $^{125}$I-OxA to HEK-OX1R with an estimated IC$_{50}$ of about 5 µM as compared to OxB (IC$^{50}$=10 nM). These results indicate that C1 and C2 antibodies specifically displace the OxA binding to its OX1R receptor.

Example 2

The inventors have tested the ability of C2 antibody to inhibit the tumor development of xenografted nude mice with the human colon adenocarcinoma cell line, HT-29. After subcutaneous injection of 1.5×10$^6$ HT-29 cells in mice, animals were treated by 2 intraperitoneal (ip) injection/week of Orexin-A (100 µg/injection corresponding to 1.4 µmoles of orexin-A/Kg) or two doses of C2 antibody (200 µg/injection or 50 µg/injection corresponding to 0.065 µmoles/Kg and 0.02 µmoles/Kg, respectively). Control was determined by ip injection of 100 µl of PBS. The experiment was conducted during 45 days and the tumor volume was estimated by measuring the short and long axes of developed-tumors each ⅔ days. As shown in FIG. 8, the inventors observed that HT-29 cells induced a tumor volume of about 1600±120 mm$^3$ (Day 43) in the absence of treatment (black circles). In contrast, injection of C2 antibody (black triangle) strongly reduced the tumor development of about 60% (tumor volume #650±98 mm$^3$) as compared to orexin treatment which induced an inhibition of about 65% (tumor volume #570±100 mm$^3$). It should be noted that the use of low dose of C2 antibody (white triangles) induced a lowest inhibition of tumor growth of 45% (tumor volume #885±130 mm$^3$) revealing a dose response relationship.

REFERENCES

Throughout this application, various references describe the state of the art to which this invention pertains. The disclosures of these references are hereby incorporated by reference into the present disclosure.

The invention claimed is:

1. An isolated human monoclonal antibody against orexin receptor type 1 (OX1R) comprising a heavy chain comprising i) the H-CDR1 of C2, ii) the H-CDR2 of C2 and iii) the H-CDR3 of C2 and a light chain comprising i) the L-CDR1 of C2, ii) the L-CDR2 of C2 and iii) the L-CDR3 of C2 wherein
the H-CDR1 of C2 is defined by the sequence ranging from the amino acid residue at position 31 to the amino acid residue at position 35 in SEQ ID NO:1,
the H-CDR2 of C2 is defined by the sequence ranging from the amino acid residue at position 50 to the amino acid residue at position 66 in SEQ ID NO:1,
the H-CDR3 of C2 is defined by the sequence ranging from the amino acid residue at position 99 to the amino acid residue at position 109 in SEQ ID NO:1,
the L-CDR1 of C2 is defined by the sequence ranging from the amino acid residue at position 23 to the amino acid residue at position 36 in SEQ ID NO:2,
the L-CDR2 of C2 is defined by the sequence ranging from the amino acid residue at position 52 to the amino acid residue at position 58 in SEQ ID NO:2, and,
the L-CDR3 of C2 is defined by the sequence ranging from the amino acid residue at position 91 to the amino acid residue at position 100 in SEQ ID NO:2.

2. The isolated human monoclonal antibody of claim 1 wherein the variable region of the heavy chain has at least 70% identity with SEQ ID NO:1, wherein any variation from SEQ ID NO:1 does not occur within H-CDR1, H-CDR-2, or H-CDR3.

3. The isolated human monoclonal antibody of claim 1 wherein the variable region of the light chain has at least 70% identity with SEQ ID NO:2, wherein any variation from SEQ ID NO:2 does not occur within L-CDR1, L-CDR-2, or L-CDR3.

4. The isolated human monoclonal antibody of claim 1 wherein the variable region of the heavy chain has at least 70% identity with SEQ ID NO:1 and wherein the variable region of the light chain has at least 70% identity with SEQ ID NO:2, wherein any variation from SEQ ID NO:1 does not occur within H-CDR1, H-CDR-2, or H-CDR3 and wherein any variation from SEQ ID NO:2 does not occur within L-CDR1, L-CDR-2, or L-CDR3.

5. The isolated human monoclonal antibody of claim 1 wherein the variable region of the heavy chain is identical to SEQ ID NO:1.

6. The isolated human monoclonal antibody of claim 1 wherein the variable region of the light chain is identical to SEQ ID NO:2.

7. The isolated human monoclonal antibody of claim 1 wherein the variable region of the heavy chain is identical to SEQ ID NO:1 and wherein the variable region of the light chain is identical to SEQ ID NO:2.

8. An isolated fragment of the isolated human monoclonal antibody of claim 1 which is selected from the group consisting of Fv, Fab, F(ab')2, Fab', dsFv, scFv, sc(Fv)2 and diabodies.

9. An isolated nucleic acid molecule which encodes the heavy chain and the light chain of the human monoclonal antibody of claim 1.

10. An isolated vector comprising the nucleic acid molecule of claim 9.

11. An isolated host cell comprising the nucleic acid molecule of claim 9.

12. A method of treating cancer in a subject in need thereof wherein cells of the cancer express OX1R comprising administering to the subject a therapeutically effective amount of the human monoclonal antibody of claim 1.

13. A pharmaceutical composition comprising the isolated human monoclonal antibody of claim 1 and a pharmaceutically acceptable carrier.

14. An isolated host cell comprising the vector of claim 10.

* * * * *